United States Patent [19]

Repplinger et al.

[11] Patent Number: 4,466,287

[45] Date of Patent: Aug. 21, 9184

[54] NON-DESTRUCTIVE, NON-CONTACT ULTRASONIC MATERIAL

[75] Inventors: Wilhelm Repplinger, Dillingen; Gerhard Hübschen, Saarlouis; Hans-Jürgen J. Salzburger, Neunkirchen, all of Fed. Rep. of Germany

[73] Assignee: Fraunhofer-Gesellschaft zur Forderung der angewandten Forschung e.V., Munich, Fed. Rep. of Germany

[21] Appl. No.: 439,310

[22] Filed: Nov. 4, 1982

[51] Int. Cl.³ ............................................. G01N 29/04
[52] U.S. Cl. ........................................ 73/643; 324/226
[58] Field of Search .................. 73/643; 324/226, 228, 324/237, 238, 240

[56] References Cited

U.S. PATENT DOCUMENTS

| 3,460,063 | 8/1969 | Houck et al. | 73/643 |
| 3,583,213 | 6/1981 | Houck et al. | 73/643 |
| 3,786,672 | 1/1974 | Gaerttner | 73/643 |
| 3,850,028 | 11/1974 | Thompson et al. | 73/643 |
| 3,918,295 | 11/1975 | Herbertz | 73/643 |
| 4,314,479 | 2/1982 | Spijkerman | 73/643 |
| 4,408,160 | 10/1983 | King et al. | 324/238 |

FOREIGN PATENT DOCUMENTS 2655804 6/1978 Fed. Rep. of Germany ........ 73/643

OTHER PUBLICATIONS

R. B. Thompson, "Noncontact Transducers", 1973 Ultrasonics Symposium Proceeding, IEEE, New York, 1973.
R. E. Beissner, Electromagnetic-Acoustic Transducers: A Survey of the State-Of-The-Art, Nondestructive Testing Information Analysis Center (NTIAC), San Antonio, Texas, Jan. 1976.
C. F. Vasile, R. B. Thompson, "Periodic Magnet Non-Contact Electromagnetic Acoustic Wave Transducer-Theory and Application", 1977 Ultrasonics Symposium Proceedings, IEEE, New York, Cat. ##77 CH1264-ISU.
H. Shimizu, A. J. Bahr, "Improved Design for Non-Contacting Electromagnetic Acoustic Transducers", 1977 Ultrasonics Symposium Proceedings, IEEE, New York, Cat. ##77 CH1264-ISU.
R. B. Thompson, "A Model for the Electromagnetic Generation of Ultrasonic Guided Waves In Ferromagnetic Metal Polycrystals", IEEE Trans. Sincs & Ultrasonics, vol. 25, No. 1, Jan. 1978.
R. B. Thompson, "New Configurations for the Electromagnetic Generation of SH Waves In Ferromagnetic Materials", 1978 Ultrasonics Symposium Proceedings, IEEE, New York, Cat. ##78 CH1344-ISU.
W. Mohr. W. Repplinger, "Elektrodynamische Beruhrungslose Anregung Freier Ultraschallwelle" Materialprufung, 20 (1978).
W. Theiner, I. Alrpeter, "Determination of Residual Stresses Using Micromagnetic Parameters", 1982. Proceeding Germany-United States Workshop on Research and Development to New Procedures in NDT, Springer Verlag Berlin, 1982.

Primary Examiner—Stephen A. Kreitman
Attorney, Agent, or Firm—Robbins & Laramie

[57] ABSTRACT

The invention relates to a method for non-contact, non-destructive testing of a test body of ferromagnetic and-/or electrically-conductive material with ultrasound waves, comprising the steps of: producing in a near-surface region of the test body a low-frequency alternating magnetic bias field having flux lines generally parallel to a surface of the test body; producing high frequency alternating magnetic excitation fields in said near-surface region generally parallel to said surface during a time interval when the bias field is at a quasi-static maximum, adjacent excitation fields having opposing polarity and having flux lines lying in mutually parallel directions, whereby ultrasound waves are generated in the test body; and detecting high frequency alternating magnetic fields in said near-surface region during the same time interval when the bias field is at a quasi-static maximum and producing a signal therefrom representative of said ultrasound waves.

In this method, the flux lines of said excitation fields lie generally parallel to the flux lines of said bias field, such that dynamic forces are electrodynamically generated in the test body in a direction normal to the surface of the test body, which launch longitudinal waves, Rayleigh waves and Lamb waves, and dynamic forces are magnetostrictively generated in the test body in a direction parallel to said surface, which launch transversal waves, Rayleigh waves and Lamb waves.

9 Claims, 11 Drawing Figures

$t_0 - t_n$: starting points of the US-wave

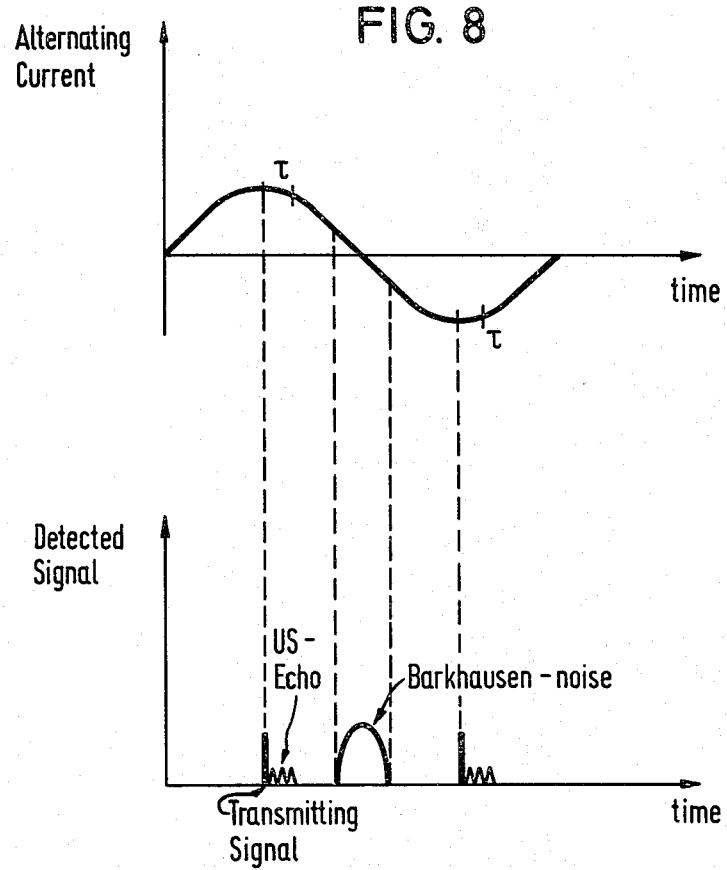
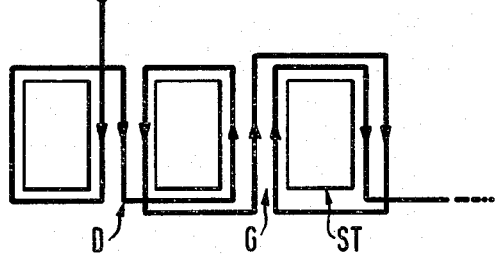

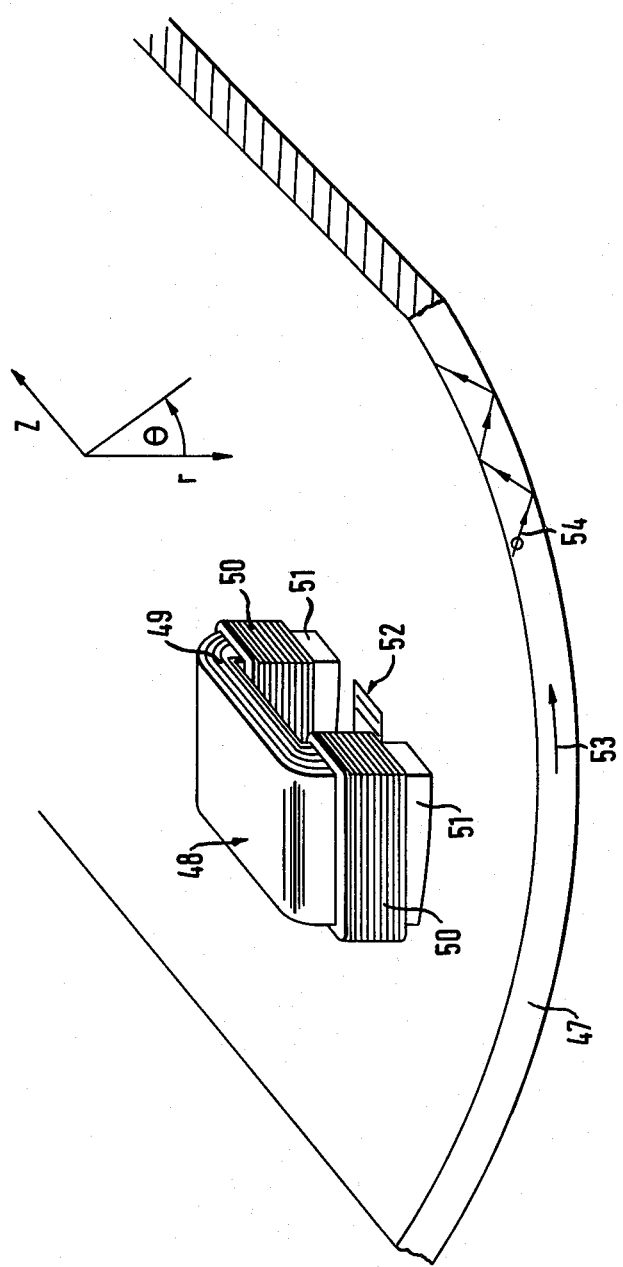

NON-DESTRUCTIVE, NON-CONTACT ULTRASONIC MATERIAL

FIELD OF THE INVENTION

The present invention relates to methods and apparatus for non-destructive, non-contact testing of materials with ultrasonic waves.

THE PRIOR ART

Ultrasonic transducers are known which produce ultrasonic (US) waves in electrically-conductive materials by electrodynamic or (in the case of ferromagnetic materials) magnetostrictive methods. Such transducers generally employ a high frequency coil in combination with a static premagnetization (static bias field) having flux lines directed either parallel to or normal to a surface of the body of material to be tested. In some cases (such as for production of shear-horizontal (SH) waves by magnetostrictive excitation and forces normal to the surface of the test body by electrodynamic excitation), a bias field having flux lines extending over relatively large distances is of interest.

Until now, permanent magnets or electromagnets with D.C. supply or pulsed direct voltage were usually employed for producing horizontal magnetic fields, i.e. fields with flux lines extending generally parallel to the surface of the test body. Examples of such arrangements are given, inter alia, in the following:

1. R. B. Thompson, "Noncontact Transducers", 1973 Ultrasonics Symposium Proceeding, IEEE, N.Y., 1973.
2. R. E. Beissner, Electromagnetic-Acoustic transducers : A survey of the state-of-the-art, Nondestructive Testing Information Analysis Center (NTIAC), San Antonio, TX, January 1976.
3. C. F. Vasile, R. B. Thompson, "Periodic magnet non-contact electromagnetic acoustic wave transducer - theory and application", 1977 Ultrasonics Symposium Proceedings, IEEE, N.Y., cat. #77 CH1264-ISU.
4. H. Shimizu, A. J. Bahr, "Improved design for non-contacting electromagnetic acoustic transducers", 1977 Ultrasonics Symposium Proceedings, IEEE, N.Y., cat #77 CH1264-ISU.
5. R. B. Thompson, "A model for the electromagnetic generation of ultrasonic guides waves in ferromagnetic metal polycrystals", IEEE Trans. Sincs & Ultrasonics, Vol. 25, No. 1, Jan. 1978.
6. R. B. Thompson, "New configurations for the electromagnetic generation of SH waves in ferromagnetic materials", 1978 Ultrasonics Symposium Proceedings, IEEE, N.Y., Cat. #78 CH1344-ISU.
7. W. Mohr, W. Repplinger, "Elektrodynamische berührungslose Anregung freier Ultraschallwelle Materialprüfung," 20 (1978).
8. U.S. Pat. No. 3,850,028 to Robert B. Thompson et al, issued Nov. 26, 1974.
9. U.S. Pat. No. 3,583,213, to James R. Houck et al, issued June 8, 1981.
10. U.S. Pat. No. 3,460,063, to James R. Houck et at, issued Aug. 5, 1969.
11. U.S. Pat. No. 3,786,672, to Martin R. Gaerttner, issued Jan. 22, 1974.
12. West German Auslegeschrift No. 26 55 804, laid open June 15, 1978.
13. W. Theiner, I. Alrpeter, "Determination of residual stresses using micromagnetic parameters", 1982. Proceeding Germany-United States Workshop on Research and Development to New Procedures in NDT, Springer Verlag Berlin, 1982.

However, static magnetic fields parallel to the surface are difficult to produce when the ratio of thickness of test body to pole distance is high, and lead to reduced efficiency.

The magnetic fields then penetrate deeply into the material. The field intensity in the near-surface region of the test body is therefore relatively low. However, for ultrasonic excitation, only the field parallel to the surface in the near-surface region is of interest; for a given magnetization power the magnetic field intensity is higher than for the same D.C.-power.

Moreover, transducers with static magnetic bias field, particularly transducers with permanent magnets, are difficult to move over the surface of a ferromagnetic test body in the event of strong fields and consequently render manipulation of the test heads (containing the bias magnet and high frequency transducer) difficult. A further drawback is that the test body may possibly become magnetized.

It is also known from U.S. Pat. No. 3,918,295 to Joachim Herbertz, issued Nov. 11, 1975, to employ high frequency transmitter coils with an electromagnet driven by a low-frequency A.C. source to produce ultrasound waves for non-destructive testing. The high frequency windings are continuously energized to generate ultrasound waves in the test piece, while the low-frequency magnet coil is continuously energized to amplitude-modulate the ultrasound waves with the low frequency magnetic fields. Received acoustic signals are separated from internal noise or external interference by detection of the amplitude modulation.

SUMMARY OF THE INVENTION

For excitation of certain ultrasonic waves in ferromagnetic and conductive test bodies, the invention provides producing a horizontal magnetic bias field in the near-surface of a test body by using a time-variable magnetic field of relatively low-frequency.

By varying the magnetic field, the flux lines of the magnetic bias field are urged into the near-surface (skin effect). By using alternating magnetic polarities the test head can thus be moved easily over the surface of the test body, even in the event of high surface field intensities. Furthermore, the test head volume can be reduced without reducing the surface field intensity of the bias field.

The time-variable magnetic field can be produced with air coils, directly magnetically coupled to the body to be tested, or with an electromagnet having a yoke core. For small magnetization losses, the magnet yoke must be composed of magnetically conductive sheets which are electrically insulated with respect to one another. The sheet thickness is determined according to the rules of A.C. transformers.

For *receiving* and *transmitting ultrasonic waves,* it is necessary according to the invention to *synchronize* transmission and reception with *magnetization.* Transmission and reception thus occur in electrodynamic transducers when the surface field intensity is at a *maximum.*

With magnetostrictive transducers, transmission and reception occur when the decrease of the magnetostriction with the magnetization field intensity is greatest. This condition is valid for most ferritic steel materials.

Synchronisation can be carried out with the aid of the energizing current of the bias field magnet. The period of time necessary for transmission and reception (path of sound) determines the maximum frequency of magnetization. It is endeavoured to transmit and receive with a field which is as constant as possible (quasistatic). This means that, during ultrasonic testing, the change in the field intensity (induction) proceeds relatively slowly.

The invention can be summarized, in one embodiment, as a method for non-contact, non-destructive testing of a test body of ferromagnetic and/or electrically-conductive material with ultrasound waves, comprising the steps of: producing in a near-surface region of the test body a low-frequency alternating magnetic bias field having flux lines generally parallel to a surface of the test body; producing high frequency alternating magnetic excitation fields in said near-surface region generally parallel to said surface during a time interval when the bias field is at a quasi-static maximum, adjacent excitation fields having opposing polarity and having flux lines lying in mutually parallel directions, whereby ultrasound waves are generated in the test body; and detecting high frequency alternating magnetic fields in said near-surface region during the same time interval when the bias field is at a quasi-static maximum and producing a signal therefrom representative of said ultrasound waves.

In this method, the flux lines of said excitation fields lie generally parallel to the flux lines of said bias field, such that dynamic forces are electrodynamically generated in the test body in a direction normal to the surface of the test body, which launch longitudinal waves, Rayleigh waves and Lamb waves, and dynamic forces are magnetostrictively generated in the test body in a direction parallel to said surface, which launch transversal waves, Rayleigh waves and Lamb waves.

BRIEF DESCRIPTION OF THE DRAWINGS

In the accompanying drawings:

FIG. 8 is a time diagram illustrating the time relations between the picking up of ultrasound and Barkhausen-noise;

FIGS. 9a and 9b show schematically a high frequency coil construction useful in practicing the present invention.

FIG. 10 shows a preferred US test head in accordance with the invention.

The preferred embodiments are described below with reference to the drawings.

THE PREFERRED EMBODIMENTS

Figure 1:
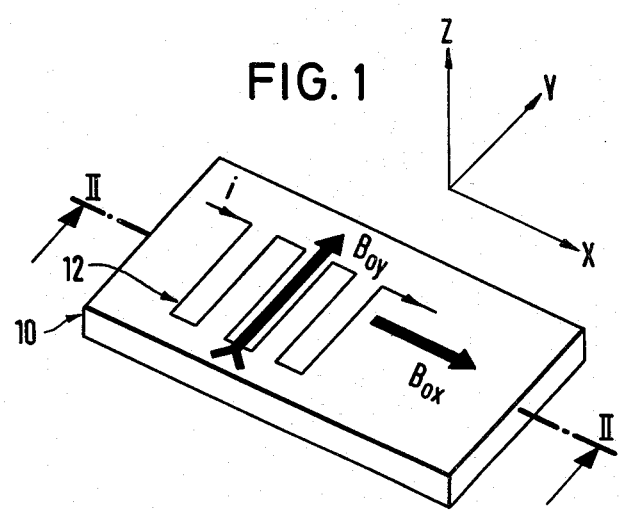
FIG. 1 shows a shematic representation of a transducer arrangement for producing US waves in a test body.

FIG. 1 illustrates a test body 10 oriented relative to a coordinate system x,y,z, such that its upper surface lies in an x-y plane. A meander-type coil 12 is situated in an x,y plane above the upper surface of the test body, and a magnetic bias field, $B_{oy}$ is produced in the upper surface of the test body in the y-direction by a magnetic yoke not shown (see FIG. 3). Coil 12 is energized with a high frequency current.

Figure 2:
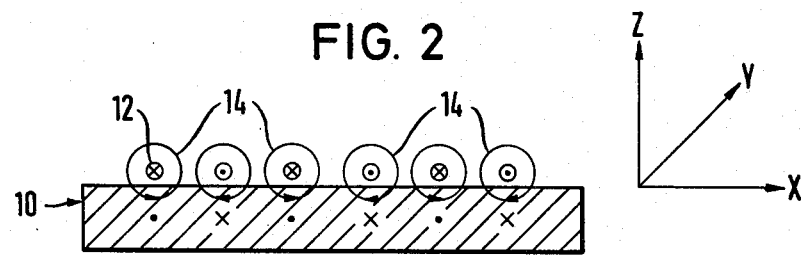
FIG. 2 is a cross-sectional view taken along line II—II of FIG. 1.

FIG. 2 shows a section of test body 10 taken along line II—II of FIG. 1. The elongate coil portions of coil 12 lie in the y-direction, producing high frequency flux lines in the x-direction in the near-surface region of the test body. The high frequency magnetic field in turn induces eddy currents in the near surface region of the conductive test body in a pattern generally resembling the configuration of coil 12. The period 14 of the coil 12 is the transducer wavelength and corresponds to the sinusoidal variation of an ultrasonic field along the x-direction.

In the presence of a bias magnetic field having flux lines in the y-direction ($B_{oy}$ in FIG. 1) magnetostrictive forces are thus applied to the metallic lattice of a ferromagnetic test body which produce shear horizontal (SH) ultrasound waves in the test body. In this case, the ultrasound waves are polarized (have components of displacement) in only the y-direction. The waves propagate in the test body in the x-and/or z directions.

If the magnetic bias field is instead oriented in the x direction ($B_{ox}$ in FIG. 1) produced by a magnetic yoke not shown (see FIG. 3) dynamic forces in the x-direction are magnetostrictively generated in a ferromagnetic test body, and dynamic forces in the Z direction are electrodynamically generated by Lorentz forces acting on the eddy currents in the test body.

Figure 3:
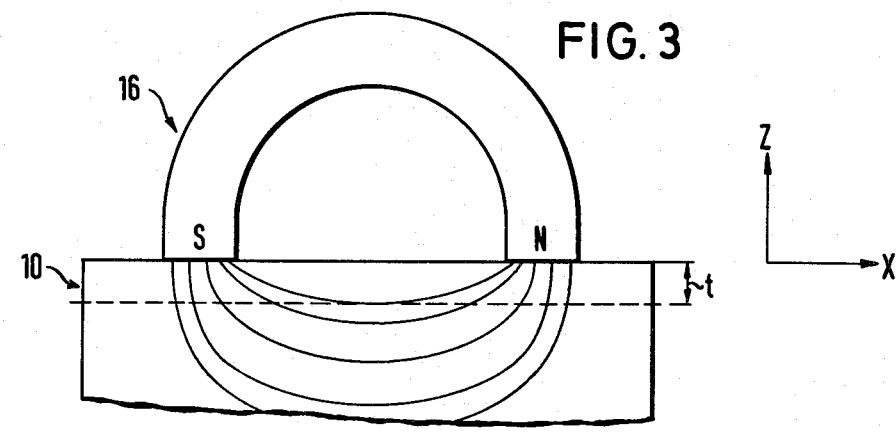
FIG. 3 shows the flux lines of a static magnetic field in a body of conductive material.

Most prior arrangements proposed for the non-contact generation of US waves employ a *static* magnetic bias field in combination with a high frequency excitation coil. The static bias field may be generated by permanent magnet or by an electromagnet energized by a D.C. or pulsed D.C. source. FIG. 3 illustrates diagramatically the static flux lines produced when such a magnet 16 is placed near a test body 10. The field penetrates relatively deeply into the test body and only a small portion of its strength in the x-direction is in the near-surface region (of thickness "t").

Figure 4:
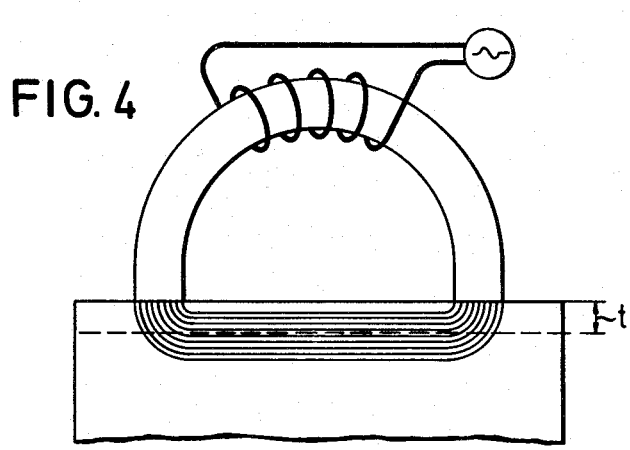
FIG. 4 shows the flux lines of an alternating magnetic field in a body of conductive material.

In contrast, FIG. 4 illustrates the flux lines of an electromagnet driven by a low frequency A.C. source. The time-varying field has a large proportion of its strength in the x-direction in the near surface region, due to skin effect. Since the near-surface flux of the magnetic bias field in the x- (or y-) direction is that which interacts with the high frequency field to produce US waves, it will be recognized that greater efficiency can be achieved with a time-varying bias field. Moreover, the magnet can be more easily moved over the surface of a ferromagnetic test body, and magnetization of the test body is avoided.

The time variable magnetic bias field may be produced by air coils situated to be directly magnetically coupled to the test body. Preferably, however, the bias field is produced by an electromagnet having a laminated yoke core. The laminations are of magnetically conductive sheets which are electrically insulated from one another. The sheet thickness is determined accordingly to the rules of A.C. transformers.

For transmitting (exciting) and receiving (detecting) US waves with a non-contact test head in accordance with the invention, it is necessary to synchronize excitation and detection of the US waves with the detection time-varying bias field strength. Thus, US wave excitation occurs with electrodynamic transducers when the near-surface bias field intensity is at a maximum.

With magnetostrictive transducers, excitation and detection occur when the decrease of the magnetostriction with the magnetization field intensity is greatest. This requirement is valid for most ferritic steel materials. Synchronization can be carried out with the aid of the energizing current of the magnet. The period of time necessary for transmission and reception (path of sound) determines the maximum frequency of magnetization. It is endeavoured to transmit and receive with a field which is as constant as possible (quasi-static). This means that, during ultrasonic testing, the change in the field intensity (induction) proceeds relatively slowly. Quasi-static means that the time interval should be smaller then 10% of the period duration of the A.C.-magnetization current. This time interval can be sufficiently long to transmit and detect more than one ultrasonic pulse.

Figure 5A:
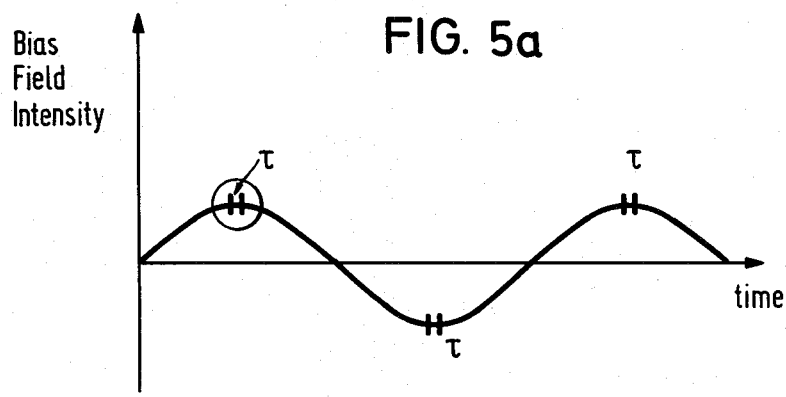
FIG. 5 is a time diagram illustrating the manner of synchronizing high frequency coil energization with the low frequency bias field in accordance with the invention.
Figure 5B:
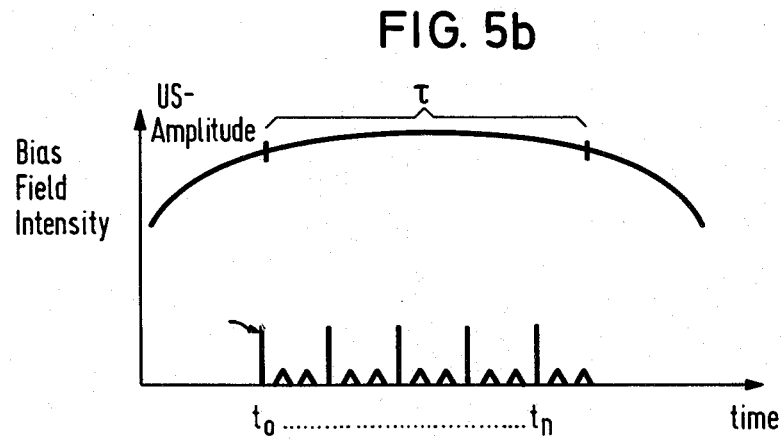

Synchronization of excitation and detection is shown diagrammatically in FIG. 5a. The high frequency coil is energized when the bias field intensity is in the region of its maximum. If interval $\tau$ is small relative to the period of the alternating bias field, the bias field strength will remain nearly unchanged during the excitation or detection. The time interval $\tau$ may be long enough to transmit and detect more than one US-pulse as shown in FIG. 5b. The first starting point $t_0$ is synchronized with the magnetization as mentioned above, the following starting points $t_1 \ldots t_n$ are given by the maximal achievable repetition rate.

Figure 6:
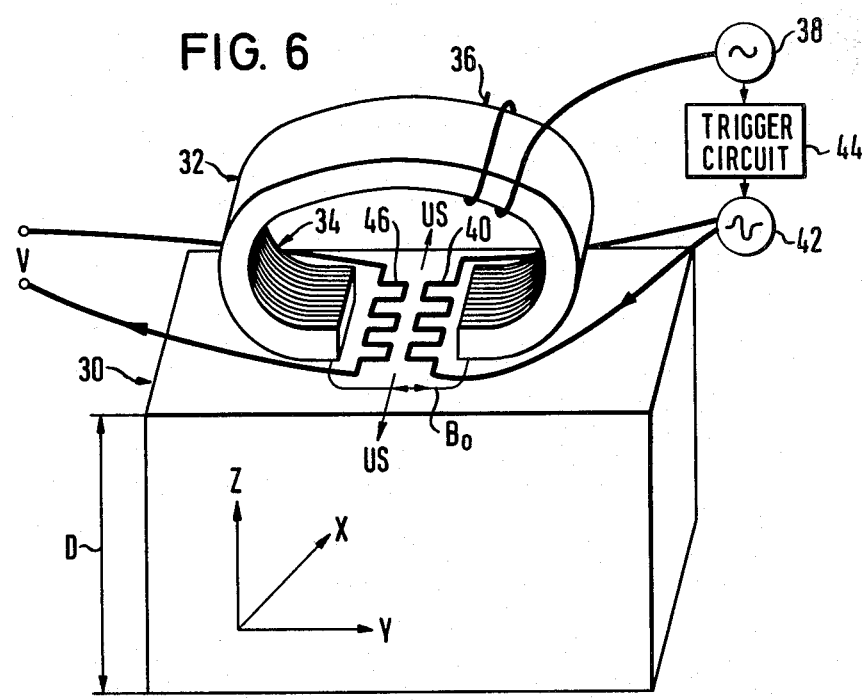
FIG. 6 shows schematically in perspective view an arrangement for ultrasonic testing of a test body in accordance with the invention.

FIG. 6 illustrates an arrangement in accordance with the invention for the ultrasonic testing of a ferromagnetic test body 30 of thickness D. An electromagnet 32 having a laminated yoke core 34 of electrically-insulated magnetically-conductive sheets is wound with a coil 36. An A.C. source 38 energizes coil 36 to continuously produce an alternating bias field in the near-surface region of test body 30. One flux line of the alternating bias field Bo lying generally parallel to the surface of body 30 is illustrated. An excitation coil 40 (which may be of any of a number of forms) lies above and generally parallel to the upper surface of the test body 30. Coil 40 is energized by a high frequency source 42 synchronized with the A.C. power source 38 by suitable trigger circuitry 44.

Figure 7A:
FIG. 7 is a time diagram illustrating the producing of the start pulses synchronized with the bias field.
Figure 7B:
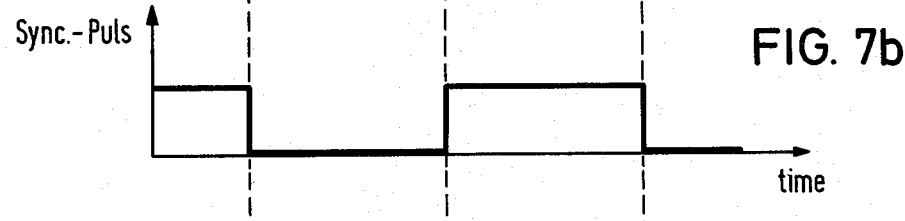
Figure 7C:
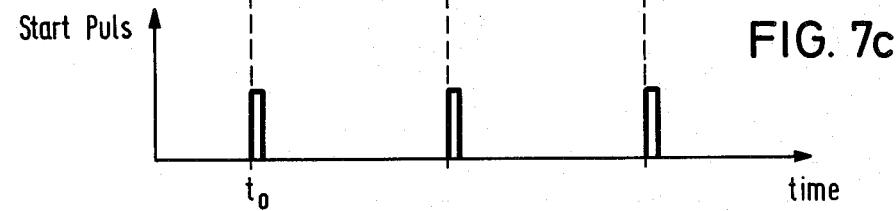

The A.C. source 38 produces a synchronization pulse (FIG. 7b) which is synchronous with the maximum of the sinus wave produced by the same generator (FIG. 7a). With the aid of the synchronization pulse and edge triggered monoflops a start pulse is produced (FIG. 7c) which triggers the high frequency source 42. This can be a tone burst or a pulse generator.

A detection coil 46 is likewise situated near the surface of body 30 adjacent the near-surface region containing the bias field $B_o$. Interaction of US waves in the test body with the bias field $B_o$ energizes detection coil 46. The output signal V from detection coil 46 is representative of the detected US waves, which generally has another shape and smaller energy than the transmitting signal and results from the reflection of the transmitted US signal at defects and geometrical obstacles.

With the arrangement of FIG. 6, the flux lines of bias field $B_o$ are parallel to the elongate portions of coil 40 (hence, normal to the flux lines produced by coil 40 in the near-surface region of test body 30), resulting in propagation of SH waves in the test body which have their direction of movement parallel to the upper body surface and their direction of propagation in the x,z-plane. The SH waves are reflected by defects or by geometrical obstacles (edges, backwall, etc) and detected at coil 46, producing an output signal.

If alternating current is used for energizing the bias field magnet, the described arrangements for ultrasonic excitation are suitable at the same time for *picking up* magnetic-inductive *Barkhausen-noises* in ferromagnetic materials (see reference no. 13 above).

The physical mechanism which produces Barkhausen noise occurs mainly near the coercive field strength of the test material; this is near the zero crossing points of the AC magnetization current. FIG. 8 shows diagrammatically the detected US-signal during time interval $\tau$ and the Barkhausen-noise during the zero crossing points of the A.C.-current for the magnetization.

It will be understood that the excitation repetition frequency is limited by the US path length, which in turn depends upon the geometry of the test body and the direction in which US waves are propagated in the test body. But the hysteresis losses increase with the magnetization frequency. The inventors have found that an A.C. source of 10 Hz-1000 Hz is suitable for energizing the bias magnet.

It is further noted that the test body need not have a strictly planar surface. For example, the test body may be a curved plate or pipe wall with a relatively large radius of curvature compared to the ultrasonic wavelength (for example, 6 mm US-wavelength, 100 mm inner radius).

In such case, the bias magnet yoke and excitation/detection coils are preferably adapted to the shape of the test body surface (e.g., curved); the bias field flux lines and excitation field flux lines are thus considered herein as being "parallel" to the surface configuration of the test body even where such surface is not strictly planar.

FIGS. 9a, b show by way of non-limiting example an excitation/detection coil configuration contemplated as being useful within the scope of the present invention. Such a configuration is known from German Patent DE-AS No. 26 55 804.

In FIG. 10, an ultrasonic test head preferred in accordance with the invention for excitation and detection of SH waves in thin, curved test bodies is shown.

At the inner surface of a pipe, a section of which is indicated at 47, a bias electromagnet with a u-formed yoke 48 consisting of laminated sheets 49 is oriented in the z-direction (e.g. the direction of the pipe axis). By means of two magnetizing coils 50 a low frequency magnetic field in the near surface region parallel to the inner surface of the pipe is produced between the two pole shoes 51. The bias magnet yoke, especially the pole shoes 51 thereof, is adapted to the inner curvature of the pipe 47. A meander-type coil 52, also adapted to the pipe curvature, is situated between the pole shoes 51. The elongate coil portions of coil 52 lie in the z-direction, producing high frequency flux lines in the near-surface region parallel to the inner surface and perpendicular to the z-direction. If the magnetizing coils 50 and the high frequency coils 52 are energized as described above, an ultrasonic wave propagates with polarization parallel to the pipe surfaces in the $\theta$,r-plane as guided SH-modes in circumferential direction 53 or as a bulk SH-wave on a zig-zag-path 54 in the pipe wall. The SH-waves are reflected by defects in the pipe wall or wall thickness reductions of the pipe wall and detected by a coil similar to coil 52 producing an output signal.

German Patent DE-AS No. 26 55 804 describes a scheme for electrically optimizing the properties of EMATs. In this context, "electrically optimum" means that, by adjusting certain parameters (e.g. the wire gauges used, transient times, wide-band character for multiplexing modes) a maximum signal-to-noise ratio is obtained.

It is within the scope of the present invention to further improve upon the operating characteristics of such EMATs by employing an alternating bias field with which excitation and detection of US waves is synchronized. Accordingly, the content of German Patent DE-AS No. 26 55 804 is incorporated herein by reference for its showing of EMAT coil arrangements in which an alternating bias field may be advantageously employed.

It is preferred that high frequency transducer coils have a configuration as shown in FIGS. 9a and 9b, wherein a coil winding D wound around a web ST n-times in grooves G in a transducer body of non-conductive material, and then wound n-times around the adjacent web so that a common direction of current flow prevails in a groove and, in the adjacent groove, the opposite direction prevails. This type of winding makes it possible to construct a transducer with greater efficiency than the simple meander-type coil shown in FIG. 1.

The foregoing preferred embodiments are given to illustrate the various ways in which the invention may be employed. Those skilled in the art will recognize other arrangements within the spirit and scope of the invention defined by the following claims.

We claim:

1. A method for non-contact, non-destructive testing of a test body of ferromagnetic and/or electrically-conductive material with ultrasound waves, comprising the steps of:
   (a) producing in a near-surface region of the test body a low-frequency alternating magnetic bias field having flux lines generally parallel to a surface of the test body;
   (b) producing high frequency alternating magnetic excitation fields in said near-surface region generally parallel to said surface during a time interval when the bias field is at a quasi-static maximum, adjacent excitation fields having opposing polarity and having flux lines lying in mutually parallel directions, whereby ultrasound waves are generated in the test body; and
   (c) detecting high frequency alternating magnetic fields in said near-surface region during the same time interval when the bias field is at a quasi-static maximum and producing a signal therefrom representative of said ultrasound waves.

2. The method of claim 1, wherein the flux lines of said excitation fields lie generally parallel to the flux lines of said bias field, such that dynamic forces are electrodynamically generated in the test body in a direction normal to the surface of the test body, which launch longitudinal waves, Rayleigh waves and Lamb waves, and dynamic forces are magnetostrictively generated in the test body in a direction parallel to said surface, which launch transversal waves, Rayleigh waves and Lamb waves.

3. The method of claim 1, wherein the flux lines of said excitation fields lie normal to the flux lines of said bias field, whereby ultrasound waves magnetostrictively generated in the test body are polarized parallel to said surface and perpendicular to their propagation direction.

4. A method for non-contact, non-destructive testing of a test body of ferromagnetic and/or electrically-conductive material with ultrasound waves, comprising the steps of:
   (a) producing in a near-surface region of the test body a low-frequency alternating magnetic bias field having flux lines generally parallel to a surface of the test body;
   (b) producing high frequency alternating magnetic excitation fields in said near-surface region in a plane generally parallel to said bias field flux lines and parallel to said surface during a time interval when the bias field is at a quasi-static maximum, adjacent excitation fields having opposing polarity and having flux lines lying in mutually parallel directions, whereby ultrasound waves are generated in the test body; and
   (c) detecting high frequency alternating magnetic fields in said near-surface region during the same time interval when the bias field is near coercive field strength, and producing a signal therefrom representative of Barkhausen noise.

5. Apparatus for non-contact, non-destructive testing of a test body of electrically-conductive and/or ferromagnetic material with ultrasound waves, comprising:
   means for producing in a near-surface region of the test-body a low frequency alternating magnetic bias field having flux lines generally parallel to a surface of the test body; and means, synchronized with said bias field means, for
   (a) producing high frequency alternating magnetic excitation fields in said near-surface region generally parallel to said surface during a time interval when the bias field is at a quasi-static maximum, adjacent excitation fields having opposing polarity and having flux lines lying in mutually parallel directions, whereby ultrasound waves are generated in the test body; and
   (b) detecting high frequency alternating magnetic fields in said near-surface region during a time interval when the bias field is at a quasi-static maximum, and producing an output signal therefrom representative of said ultrasound waves.

6. The apparatus according to claim 5, wherein said bias field means comprises an electromagnet having a laminated yoke core, and a coil winding about said core.

7. The apparatus according to claim 6, wherein said bias field means further comprises a low frequency signal source coupled for energizing said coil winding.

8. The apparatus according to claim 5, wherein said synchronized means includes at least one transducer having:
   a non-conductive transducer body with a plurality of elongated and mutually parallel webs separated by grooves, and
   coil windings wound a plurality of times around the webs such that current in portions of the windings lying in each groove flows in a uniform direction and that current in portions of windings lying in adjacent grooves flows in opposing directions.

9. The apparatus according to claim 5, wherein said synchronized means further includes a high frequency signal generator, coupled to a first said transducer and to said bias field producing means, for energizing said transducer coil windings when said bias field is at a quasi-static maximum.

* * * * *